US00PP25359P3

(12) United States Plant Patent
Khemakongkanond

(10) Patent No.: US PP25,359 P3
(45) Date of Patent: Mar. 17, 2015

(54) ***AGLAONEMA* PLANT NAMED 'KKAG201302'**

(50) Latin Name: *Aglaonema commutatum*
Varietal Denomination: KKAG201302

(71) Applicant: Kanachana Khemakongkanond, Bangkok (TH)

(72) Inventor: Kanachana Khemakongkanond, Bangkok (TH)

( * ) Notice: Subject to any disclaimer, the term of this patent is extended or adjusted under 35 U.S.C. 154(b) by 139 days.

(21) Appl. No.: 13/815,761

(22) Filed: Mar. 14, 2013

(65) Prior Publication Data

US 2014/0283267 P1 Sep. 18, 2014

(51) Int. Cl.
*A01H 5/00* (2006.01)

(52) U.S. Cl.
USPC ..... Plt./376

(58) Field of Classification Search
USPC ..... Plt./376
See application file for complete search history.

*Primary Examiner* — Anne Grunberg

(57) ABSTRACT

A new and distinct *Aglaonema* cultivar named 'KKAG201302' is disclosed, characterized by leaves of ovate shape and pink, cream, and green color. The new variety is an *Aglaonema*, typically produced as an indoor ornamental plant.

1 Drawing Sheet

Latin name of the genus and species: *Aglaonema commutatum.*

Variety denomination: 'KKAG201302'.

BACKGROUND OF THE INVENTION

The new cultivar is the product of chance discovery. The new variety originated as a naturally occurring whole plant mutation of unpatented, proprietary *Aglaonema commutatum* referred to as 'JAY001'.

The new variety was first selected by the inventor, Kanchana Khemakongkanond, a citizen of Thailand, in May of 2009 at a nursery in Bangkok, Thailand. After identifying the new variety as a potentially interesting selection, the inventor continued confidential testing and propagation of 'KKAG201302', assessing stability of the unique characteristics of this variety.

Asexual reproduction of the new cultivar 'KKAG201302' by vegetative cuttings was first performed at the same nursery in Bangkok, Thailand during June of 2010 Subsequently many generations have been produced from vegetative cuttings, and have shown that the unique features of this cultivar are stable and reproduced true to type.

SUMMARY OF THE INVENTION

The cultivar 'KKAG201302' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KKAG201302'. These characteristics in combination distinguish 'KKAG201302' as a new and distinct *Aglaonema* cultivar:

1. Pink, cream, and green colored leaves.
2. Ovate leaf shape.

PARENT COMPARISON

Plants of the new cultivar 'KKAG201302' are similar to the parent variety, in most horticultural characteristics. The new cultivar, however, produces leaves that are more round in shape than those of the parent. Additionally the new cultivar produces a leaf of more color speckling, and of brighter color than those of the parent.

COMMERCIAL COMPARISON

Plants of the new cultivar 'KKAG201302' are comparable to the unpatented variety *Aglaonema* 'Dud Unyamanee'. The two *Aglaonema* varieties are similar in most horticultural characteristics; however, the new cultivar 'KKAG201302' produces leaves that are of different shape than those of comparator 'Dud Unyamanee'. The leaves of 'KKAG201302' are of different red coloration as well as having less pink coloration than those of comparator 'Dud Unyamanee'.

Plants of the new cultivar 'KKAG201302' ca also be compared to the unpatented variety *Aglaonema* 'Valentine'. The two *Aglaonema* varieties are similar in most horticultural characteristics; however, the new cultivar 'KKAG201302' produces leaves of a different shape than those of comparator 'Valentine'. The leaves of 'KKAG201302' are of different red coloration as well as having less pink coloration than those of comparator 'Valentine'. Additionally, the main veins of 'KKAG201302' are lighter in color than those of comparator 'Valentine'.

BRIEF DESCRIPTION OF THE PHOTOGRAPH

The accompanying photograph in FIG. 1 illustrates in full color a typical plant of 'KKAG201302' grown in a commercial greenhouse in Honselersdijk, The Netherlands. This plant is approximately 8 months old shown planted in 15 cm container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'KKAG201302' plants grown according to the following protocols.

Plants were grown in Honselersdijk, the Netherlands under controlled greenhouse conditions, with temperatures ranging approximately from 20° C. to 22° C. during the day and 18° C. to 20° C. at night with natural sunlight. Measurements and numerical values below represent averages of typical plant types.

Botanical classification: *Aglaonema Commutatum* 'KKAG201302'.

PROPAGATION

First propagation method: Cuttings.
Type of propagation typically used: Cuttings.
Time to initiate roots: About 14 days at approximately 21° C.
Root description: Moderately dense, moderately thick, non-fibrous, fleshy, not free-branching, colored greyed-orange; near RHS-CC 165C.
Time to produce rooted plantlet: Approximately 10 weeks at approximately 20 to 22° C.

PLANT

Age of plant described: Approximately 8 months.
Growth habit: Broad upright.
Plant shape: Obovate.
Height: Approximately 22.3 cm to top of highest leaf.
Plant spread: Approximately 19.9 cm in a 12 cm circular pot.
Normal pot size: 12 cm circular pot.
Growth rate: Moderate.
Branching characteristics: Basal branching, no lateral branches.
Number of clumps of leaves: 1.
Number of leaves per clump: Average 12.
Number of leaves per plant: Approximately 12.

FOLIAGE

Leaf:
- *Arrangement*.—Irregular basal emerging.
- *Average length(excluding petiole)*.—Approximately 10.2 cm.
- *Average width*.—Approximately 7.5 cm.
- *Shape of blade*.—Ovate to broad ovate.
- *Aspect*.—Leaves outward to slightly upright.
- *Apex*.—Apiculate.
- *Base*.—Cordate.
- *Margin*.—Entire, slightly undulate.
- *Texture of top surface*.—Smooth, slightly glossy.
- *Texture of bottom surface*.—Smooth, slightly glossy.
- *Color*.—Young foliage upper side: Red; near RHS 54B and 54C, lighter towards the base; near RHS 56B. Irregular margins and blotches green and yellow-green; near RHS 143A and 144B. Blotched white; near NN155A and NN155B. Young foliage under side: Red; near RHS 54C and 54D, lighter towards the base; near RHS 56D. Irregular margins and blotches green and yellow-green; near RHS 143A and 144C. Blotched white; near NN155A. Mature foliage upper side: Red and greyed-red; near RHS 47A and 180A, irregular margins and blotches green and yellow-green; near RHS 139A and 144A. Blotched white and yellow-green; near 155A, 155B, 155C, 155D and 145C and 145D. Mature foliage under side: Red to greyed-red; a color between RHS 181D and 54D Irregular margins and blotched green and yellow-green; near RHS N137B and 144C. Blotched yellow-green and green-white; near RHS 150D and 157C.

Venation:
- *Type*.—Pinnate.
- *Venation coloration upper side*.—Yellow-green; near RHS 147A.
- *Venation coloration under side*.—Yellow-green; near RHS 147B and 148B.

Sheath:
- *Average length*.—Approximately 4.8 cm.
- *Average width*.—Approximately 0.6 cm.
- *Color*.—Yellow-green; near RHS 149D, blotched green; near RHS 143A and 143B.
- *Texture*.—Smooth, dull.

Young petiole:
- *Length*.—Approximately 5.4 cm.
- *Width*.—At distal end: Approximately 0.4 cm. Above clump: Approximately 0.8 cm.
- *Color*.—Green; near RHS 137B, more towards yellow-green near the base; near RHS 143A.
- *Strength*.—Strong.

Mature petiole:
- *Diameter*.—0.7 cm.
- *Length*.—6.5 cm.
- *Color*.—Yellow-green; near RHS 147A.
- *Texture*.—Smooth, moderately glossy.

FLOWERING CHARACTERISTICS

Flowering not observed to date.

REPRODUCTIVE ORGANS

Not observed to date.

OTHER CHARACTERISTICS

Disease resistance: Good resistance to the normal diseases found in *Aglaonema*.
Drought tolerance and cold tolerance: Normal for species, USDA zone 10 and higher.
Fruit/seed production: No fruits/seeds detected to date.

What is claimed is:

1. A new and distinct cultivar of *Aglaonema* plant named 'KKAG201302' as herein illustrated and described.

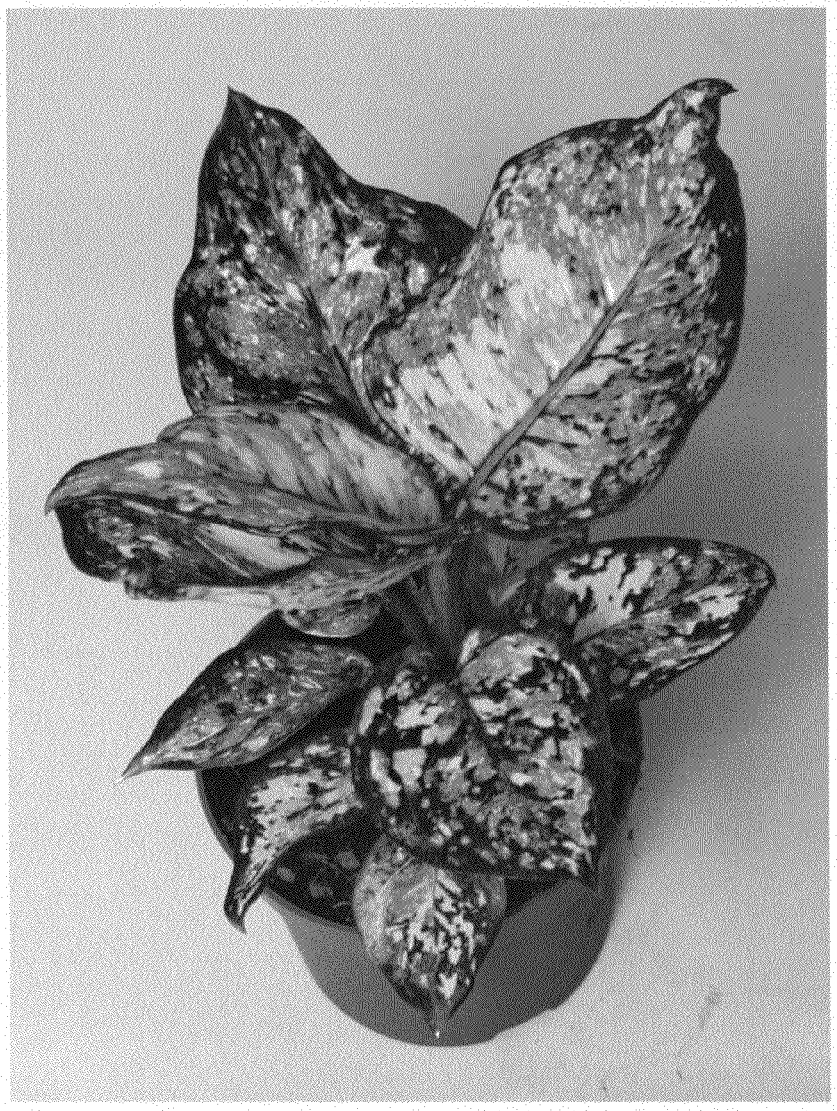

* * * * *